(12) United States Patent
Umebayashi (10) Patent No.: US 8,382,928 B2
(45) Date of Patent: Feb. 26, 2013

(54) METHOD FOR MANUFACTURING PANTS-TYPE DIAPER

(75) Inventor: Toyoshi Umebayashi, Osaka (JP)

(73) Assignee: Zuiko Corporation, Osaka (JP)

( * ) Notice: Subject to any disclaimer, the term of this patent is extended or adjusted under 35 U.S.C. 154(b) by 189 days.

(21) Appl. No.: 13/000,716

(22) PCT Filed: Sep. 8, 2009

(86) PCT No.: PCT/JP2009/004425
§ 371 (c)(1),
(2), (4) Date: Dec. 22, 2010

(87) PCT Pub. No.: WO2010/032396
PCT Pub. Date: Mar. 25, 2010

(65) Prior Publication Data
US 2011/0100536 A1    May 5, 2011

(30) Foreign Application Priority Data

Sep. 19, 2008   (JP) ................................ 2008-240414

(51) Int. Cl.
*A61F 13/15* (2006.01)
(52) U.S. Cl. .................. 156/204; 156/226; 604/385.01; 604/386
(58) Field of Classification Search .................. None
See application file for complete search history.

(56) References Cited

U.S. PATENT DOCUMENTS

| 5,855,574 | A | 1/1999 | Kling et al. | |
|---|---|---|---|---|
| 6,432,243 | B1 | 8/2002 | Popp et al. | |
| 6,635,135 | B2 * | 10/2003 | Kuen et al. | 156/199 |
| 6,830,566 | B2 * | 12/2004 | Kuen et al. | 604/396 |
| 6,936,129 | B2 * | 8/2005 | Karami et al. | 156/265 |
| 7,459,050 | B2 * | 12/2008 | Karlsson et al. | 156/204 |
| 2002/0111596 | A1 | 8/2002 | Fletcher et al. | |
| 2009/0043275 | A1 | 2/2009 | Perneborn | |

FOREIGN PATENT DOCUMENTS

| EP | 0 320 989 | 1/2001 |
|---|---|---|
| EP | 1 523 968 | 4/2005 |
| JP | 2-140163 | 5/1990 |
| JP | 9-511426 | 11/1997 |
| WO | WO 2007004640 A1 * | 1/2007 |

OTHER PUBLICATIONS

International Search Report for corresponding International Application No. PCT/JP2009/004425 mailed Dec. 22, 2009.

* cited by examiner

*Primary Examiner* — Babara Musser
(74) *Attorney, Agent, or Firm* — Renner, Otto, Boisselle & Sklar, LLP (57) ABSTRACT

A method for manufacturing a pants-type diaper of the present invention includes: a step of carrying a diaper body in a longitudinal direction X; a first folding step of folding a side panel 3 along a first line L1 extending in the longitudinal direction; a first attachment step of attaching first end portions 31 of a pair of side panels 3 to end portions 20a (21a), opposing each other in a girth direction Y, of the front portion 20 or the back portion 21; a second folding step of folding the diaper body 2 along a second line L2 extending along the girth direction Y so that the front portion 20 and the back portion 21 lie on each other; and a second attachment step of attaching second end portions 32 of the pair of side panels 3 to end portions, opposing each other in the girth direction Y, of the back portion 21 or the front portion 20, to which the side panel 3 has not been attached in the first attachment step.

4 Claims, 4 Drawing Sheets

METHOD FOR MANUFACTURING PANTS-TYPE DIAPER

TECHNICAL FIELD

The present invention relates to a method for manufacturing a pants-type diaper.

BACKGROUND ART

There has been proposed in the prior art a method for manufacturing a pants-type diaper, including: continuously carrying a plurality of diaper bodies which have not been separated from one another; attaching side panels to opposing end portions of the front side and the back side of the diaper body; cutting it into separate diaper bodies; folding up the diaper body along the crotch portion; and attaching the side panels of the front side and the side panels of the back side to each other (see the first patent document).

CITATION LIST

Patent Document

FIRST PATENT DOCUMENT: Japanese Laid-Open Patent Publication No. 2-140163 (FIGS. 2, 5 and 6)

SUMMARY OF INVENTION

In the first patent document, since the side panels of the front side and the back side are attached to each other, the attachment portions are formed on the sides of the waist of the wearer. Therefore, the attachment portions protrude outwardly to thereby deteriorate the appearance, and where the wearer lies on their side, the rigid attachment portion strongly contacts the waist side of the wearer, thereby giving the wearer discomfort.

When packaging the conventional pants-type diaper, if it is folded up so that the side panels are pushed in between the front side and the back side of the diaper body, the rigid attachment portions of the side panels hinder the pushing in, making it difficult to neatly fold up the diaper.

It is therefore an object of the present invention to provide a method for manufacturing a pants-type diaper which has desirable appearance and good wearability even when the wearer lies on their side, and which can be folded up neatly.

In order to achieve the object, a method for manufacturing a pants-type diaper of the present invention is a method for manufacturing a pants-type diaper including: a diaper body including a front portion covering an abdominal side of a wearer, a back portion covering a back side of the wearer, and a crotch portion between the front portion and the back portion; a side panel connecting together, in a girth direction, a first side edge portion (a side edge portion) of the front portion and a first side edge portion (a side edge portion) of the back portion with each other; and another side panel connecting together, in the girth direction, a second side edge portion (another side edge portion) of the front portion which is away from the first side edge portion thereof in the girth direction and a second side edge portion (another side edge portion) of the back portion which is away from the first side edge portion thereof in the girth direction, the method comprising: a step of carrying the diaper body in a longitudinal direction perpendicular to the girth direction; a first folding step of folding each of the side panels along a virtual first line extending in the longitudinal direction so that a first portion and a second portion of each of the side panels lie on each other; a first attachment step of attaching a first end portion of each of the side panels in the girth direction to the first and second side edge portions of the front portion or attaching the first end portion of each of the side panels in the girth direction to the first and second side edge portions of the back portion; a second folding step of folding the diaper body along a virtual second line extending along the girth direction so that the front portion and the back portion lie on each other; and a second attachment step of attaching a second end portion of each of the side panels away from the first end portion thereof in the girth direction to the first and second side edge portions of the back portion, to which each of the side panels is unattached in the first attachment step or attaching the second end portion of each of the side panels to the first and second side edge portions of the front portion, to which each of the side panels is unattached in the first attachment step According to the present invention, since the pre-folded side panels are attached between the front portion and the back portion, there is no portion where the side panels are attached to each other, as opposed to a case where two side panels, which are attached respectively to the front portion and to the back portion, are attached to each other. Therefore, when worn, there will be no such attachment portion protruding outside. Thus, the appearance is desirable.

There is no attachment portion where side panels are attached to each other. Therefore, even if the wearer lies on their side, no attachment portion contacts the waist side of the wearer. This results in desirable wearability.

Moreover, where when packaging, the side panel is folded up by being pushed in between the front side and the back side of the diaper body, it is possible to neatly fold up the pants-type diaper by folding up the single side panel having no attachment portion by pushing it in.

In the present invention, it is preferred that the method further includes a tentative fastening step of tentatively fastening together the first portion and the second portion of each of the side panels in order to maintain the folded state of each of the side panels which has been folded in the first folding step.

In this embodiment, the folded state of the side panel is maintained by the tentative fastening. Therefore, it is possible to reliably attach the side panels, which have been folded in the first folding step, and the diaper body to each other in the second attachment step.

In the present invention, the method may be configured so that each of the side panels is folded in the first folding step so that skin-contact surfaces thereof face each other; and each of the side panels is attached to the front portion and the back portion in the first and second attachment steps so that a portion of each of the side panels other than the first and second end portions projects out from the diaper body.

In this case, most of the side panel is projecting from the diaper body, and there is therefore a large space inside the diaper. Thus, it is easy to put the legs through the diaper.

In the present invention, the "skin-contact surface of a side panel" refers to the inner surface of the side panel which comes into direct or indirect contact with the skin of the wearer when the diaper is worn.

In the present invention, the method may be configured so that each of the side panels is folded in the first folding step so that non-skin-contact surfaces thereof face each other; and each of the side panels is attached to the front portion and the back portion in the first and second attachment steps so that at least a portion of each of the side panels between the first end portion and the second end portion is sandwiched between the front portion and the back portion.

In this case, since the side panels are not projecting from the diaper body, the packaged state is compact.

In the present invention, the "non-skin-contact surface of a side panel" refers to the outer surface of the side panel which is opposite to the skin-contact surface and which does not come into contact with the skin of the wearer.

In the present invention, the method may further include: a step of placing each of the side panels on the diaper body so that the first and second end portions of each of the side panels folded in the first folding step protrude from each of the side edge portions of the diaper body in the girth direction; a step of folding back the first end portion of each of the side panels so that the first end portion each lies on the first and second side edge portions of the diaper body in the girth direction; and a step of folding back the second end portion of each of the side panels so that the second end portion each lies on the first and second side edge portions of the diaper body in the girth direction, wherein the folded-back first end portion is attached to the diaper body in the first attachment step and the folded-back second end portion is attached to the diaper body in the second attachment step.

In this embodiment, it is easier for the wearer to put the legs through by flipping back the folded portions of the side panels which are folded along the first line when wearing the diaper.

It is preferred that in the tentative fastening step, the first portion and the second portion of each of the folded side panels are tentatively fastened together as well as each of the side panels is tentatively fastened to the diaper body to thereby prevent the side panels from slipping out of place with respect to the diaper body.

In this embodiment, the tentative fastening between the first portion and the second portion of the side panel and the tentative fastening between the side panel and the diaper body can be done in a single step, thereby reducing the number of fastening steps.

In the present invention, the method may be configured so that the diaper bodies are carried in a form of a first continuous web in which a plurality of diaper bodies are unseparated from one another; the side panels are carried in a form of a second continuous web in which a plurality of side panels are unseparated from one another; the second continuous web is cut into a continuous panel including two side panels continuous with each other which are to be attached to the diaper bodies adjacent with each other in the first continuous web; the cut-off continuous panel is attached to the first continuous web; and the first continuous web is cut, together with the continuous panel, along a virtual third line, which bisects the continuous panel in the girth direction, so as to cut the first continuous web into individual diaper bodies.

In this case, the continuous panels including two side panels continuous with each other are placed on the first continuous web, thereby reducing the number of iterations of the carrying step for placement.

DESCRIPTION OF EMBODIMENTS

The present invention will be understood more clearly from the following description of preferred embodiments taken in conjunction with the accompanying drawings. Note however that the embodiments and the drawings are merely illustrative and should not be taken to define the scope of the present invention. The scope of the present invention shall be defined only by the appended claims. In the accompanying drawings, like reference numerals denote like components throughout the plurality of figures.

Embodiment 1

Embodiments of the present invention will now be described with reference to the drawings.

Figure 1:
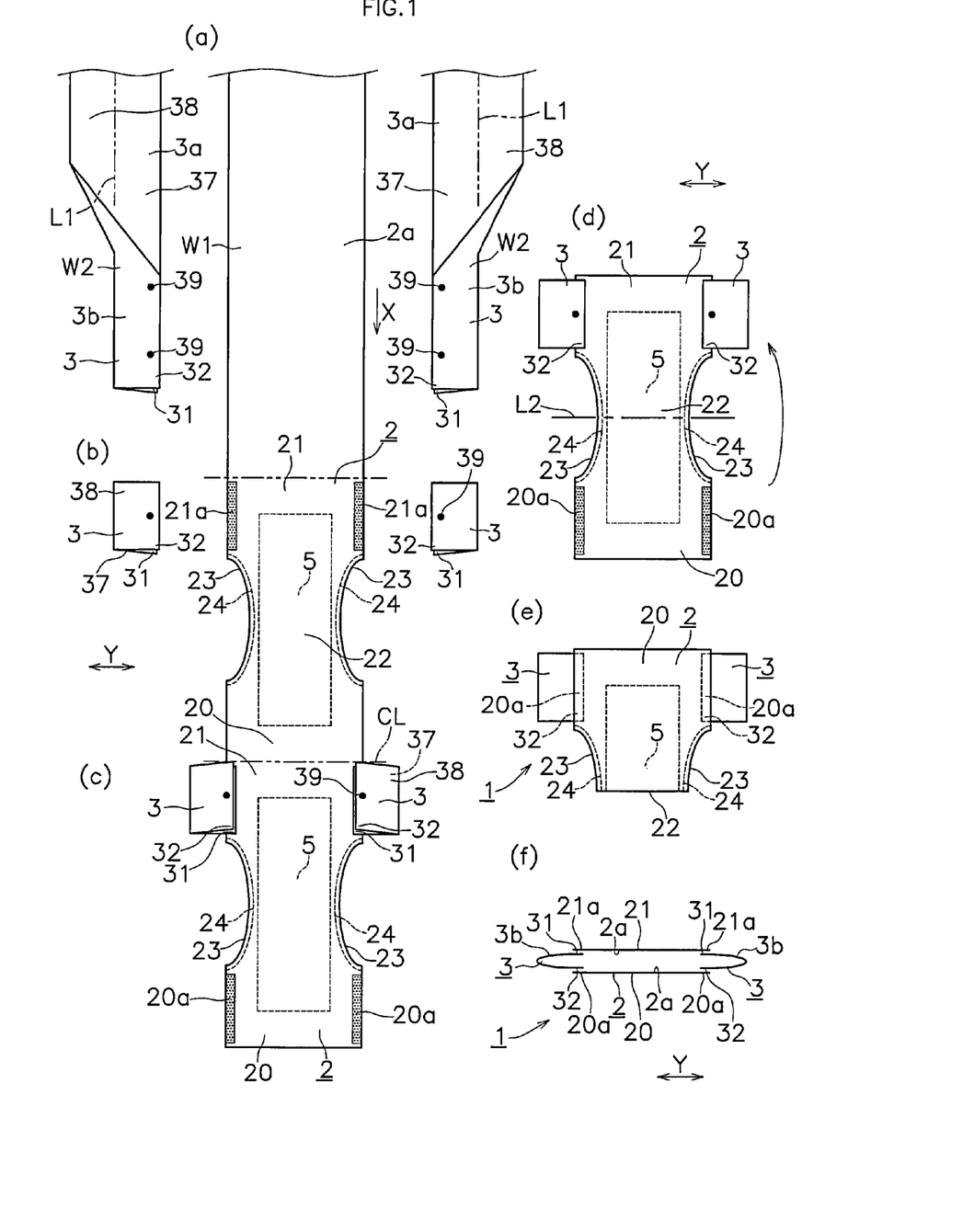
FIGS. 1(a) to 1(e) are schematic front views showing a method for manufacturing a pants-type diaper according to Embodiment 1 of the present invention.
FIG. 1(f) is a schematic cross-sectional view showing the pants-type diaper.

FIG. 1 shows Embodiment 1.

Pants-Type Diaper 1:

As shown in FIGS. 1(e) and 1(f), a pants-type diaper 1 of Embodiment 1 includes a diaper body 2 and side panels 3. The diaper body 2 includes a front portion 20 covering the front side of the wearer, a back portion 21 covering the back side of the wearer, and a crotch portion 22 between the front portion 20 and the back portion 21. A pair of side panels 3 are provided at opposing side edge portions 20a and 21a of the diaper body 2 so as to connect together the front portion 20 and the back portion 21 in a girth direction Y.

Next, a method for manufacturing the pants-type diaper 1 will be described.

Step of Carrying Diaper Body 2:

As shown in FIG. 1(a), the diaper bodies 2 are carried in the form of a first continuous web W1 in which a plurality of diaper bodies 2 are continuous together (not separated from one another).

The first continuous web W1 is formed by a continuous laminate sheet, for example, and is carried in a longitudinal direction (carrying direction) X generally perpendicular to the girth direction Y.

The diaper body 2 is provided with an absorbent body 5 covering the crotch of the wearer, etc.

The diaper body 2 may be provided with around-leg portions 23 which are cut so as to conform to leg portions of the wearer. The around-leg portions 23 may be provided with elastic members 24 formed by rubber threads, for example, so that they conform to the legs of the wearer.

The front portion 20 and the back portion 21 of the diaper body 2 may be provided with an elastic member for making the diaper 1 fit the wearer. The elastic member may be, for example, a plurality of rubber threads or rubber tapes, or a material including a film or a thermoplastic resin.

First Folding Step:

On the other hand, the side panels 3 are separately carried in the form of a pair of second continuous webs W2 each including a plurality of side panels 3 continuous together.

The side panel 3 is folded along a first line L1 extending in a carrying direction X of the side panel 3 so that a first portion 37 and a second portion 38 of the side panel 3 lie on each other. That is, the side panel 3 is folded so that skin-contact surfaces 3a thereof face each other. The opposing side panels 3 are folded so that their first and second end portions 31 and 32 are closer to the diaper body 2.

Tentative Fastening Step:

In order to maintain the folded state of the side panel 3 which has been folded in the first folding step, the first portion 37 and the second portion 38 of the side panel 3 are tentatively fastened together by heat seal, or the like, for example, at a tentatively-fastened portion 39. Note that the tentative fastening is done in a dot pattern so that they can be easily separated when wearing the diaper.

Then, as shown in FIG. 1(b), the tip portion of the second continuous web W2 in the carrying direction X is cut off so as to cut the second continuous web W2 into individual side panels 3.

First Attachment Step:

On the other hand, an adhesive is applied on the opposing side edge portions 21a on the side of a skin-contact surface 2a of the back portion 21 of the diaper body 2. As shown in FIG. 1(c), the first end portions (one of the end portions) 31 of the pair of side panels 3 are attached respectively to the side edge portions 21a, opposing each other in the girth direction Y, of the back portion 21 of the diaper body 2. Note that prior to the attachment, the first end portions 31 are placed on the diaper body 2 so that the opposing side panels 3 protrude from the diaper body 2 in the girth direction Y.

Then, the first continuous web W1 is cut along a cut-off line CL generally parallel to the girth direction Y into individual diaper bodies 2.

Second Folding Step:

After an adhesive is applied on the opposing side edge portions 20a of the skin-contact surface 2a on the side of the front portion 20 of the diaper body 2, the diaper body 2 is folded in two along a second line L2 extending along the girth direction Y shown in FIG. 1(d). The second line L2 is set at a position such that the front portion 20 and the back portion 21 lie on each other (in line symmetry with each other).

Second Attachment Step:

As the diaper body 2 is folded, the second end portions (the other end portions) 32 of the pair of side panels 3 are attached to the side edge portions 20a, opposing each other in the girth direction Y, of the front portion 20 of the diaper body 2, as shown in FIG. 1(e).

Therefore, the second end portions 32 of the side panels 3 are attached to the front portion 20, to which the side panels 3 have not been attached in the first attachment step.

As shown in FIGS. 1(e) and 1(f), a pants-type diaper manufactured by the manufacturing method described above has the side panels 3 projecting from the diaper body 2 in the girth direction Y.

Note that while the diaper body 2 is carried with the front portion 20 on the downstream side in the above description, the diaper body 2 may be carried with the back portion 21 on the downstream side.

The adhesive may be an adhesive formed by a hotmelt resin, for example.

Moreover, an adhesive may be applied simultaneously on the opposing side edge portions 20a on the side of the front portion 20 and the opposing side edge portions 21a on the side of the back portion 21.

The method for attaching the side panels 3 to the diaper body 2 may be a heat seal method, an ultrasonic method, or the like, as well as the method using an adhesive.

Embodiment 2

Figure 2:
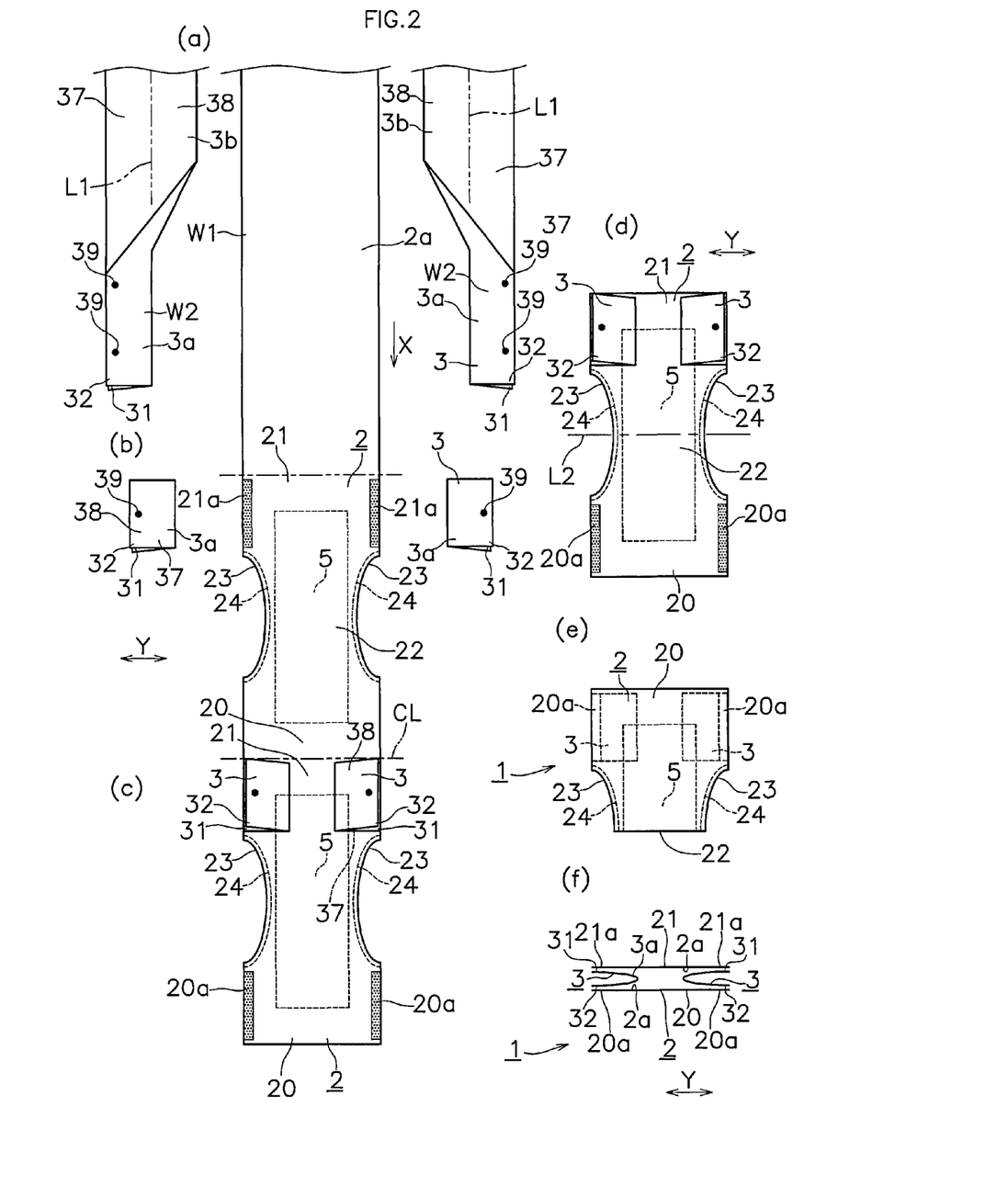
FIGS. 2(a) to 2(e) are schematic front views showing a method for manufacturing a pants-type diaper according to Embodiment 2 of the present invention.
FIG. 2(f) is a schematic cross-sectional view showing the pants-type diaper.

FIG. 2 shows Embodiment 2.

A pants-type diaper of Embodiment 2 is formed so that the side panels 3 are sandwiched between the front portion 20 and the back portion 21 of the diaper body 2, as shown in FIGS. 2(e) and 2(f). The first and second end portions 31 and 32 of the side panels 3 are attached to the end portions 21a and 20a of the back portion 21 and the front portion 20 of the diaper body 2 on the side of the skin-contact surface 2a.

The diaper manufacturing method will now be described.

Step of Carrying Diaper Body 2:

As shown in FIG. 2(a), the diaper bodies 2 are carried in the form of a first continuous web W1 in which a plurality of diaper bodies 2 are not separated from one another.

First Folding Step:

On the other hand, the side panels 3 are separately carried in the form of a pair of second continuous webs W2 each including a plurality of side panels 3 not separated from one another.

The side panel 3 is folded along the first line L1 extending in the carrying direction X so that the non-skin-contact surfaces (outer surface) 3b of the side panels 3 face each other.

The opposing side panels 3 are folded so that portions near the first line L1 are closer to the diaper body 2. That is, they are folded so that the first and second end portions 31 and 32 are away from the diaper body 2.

Tentative Fastening Step:

In order to maintain the folded state of the side panel 3 which has been folded in the first folding step, the first portion 37 and the second portion 38 of the side panel 3 are tentatively fastened together by heat seal, or the like, for example, at the tentatively-fastened portion 39.

Then, as shown in FIG. 2(b), the second continuous web W2 is cut into individual side panels 3 which are carried with a predetermined interval therebetween.

First Attachment Step:

On the other hand, after an adhesive is applied on the opposing side edge portions 21a of the back portion 21 of the diaper body 2 on the side of the skin-contact surface 2a, the side panels 3 are placed on the diaper body 2 as shown in FIG. 2(c). As the side panels 3 are placed on the diaper body 2, the first end portions 31 of the pair of side panels 3 are attached to the side edge portions 21a, opposing each other in the girth direction Y, of the back portion 21 of the diaper body 2.

Then, the first continuous web W1 is cut into individual diaper bodies 2 as shown in FIG. 2(c) along the cut-off line CL generally parallel to the girth direction Y.

Second Folding Step:

Then, after an adhesive is applied on the opposing side edge portions 20a of the front portion 20 of the diaper body 2 on the side of the skin-contact surface 2a, the diaper body 2 is folded along the second line L2 extending along the girth direction Y shown in FIG. 2(d).

Second Attachment Step:

As the diaper body 2 is folded, the second end portions 32 of the pair of side panels 3 are attached to the side edge portions 20a, opposing each other in the girth direction Y, of the front portion 20 of the diaper body 2.

Therefore, in the second attachment step, the second end portions 32 of the pair of side panels 3 are attached to the front portion 20, to which the side panels 3 have not been attached.

A pants-type diaper manufactured by the manufacturing method described above is in a compact state where the side panels 3 are sandwiched between the front portion 20 and the back portion 21 as shown in FIGS. 2(e) and 2(f).

Other than this, the configuration is similar to that of Embodiment 1, and like elements are denoted by like reference numerals and will not be described below.

Embodiment 3

Figure 3:
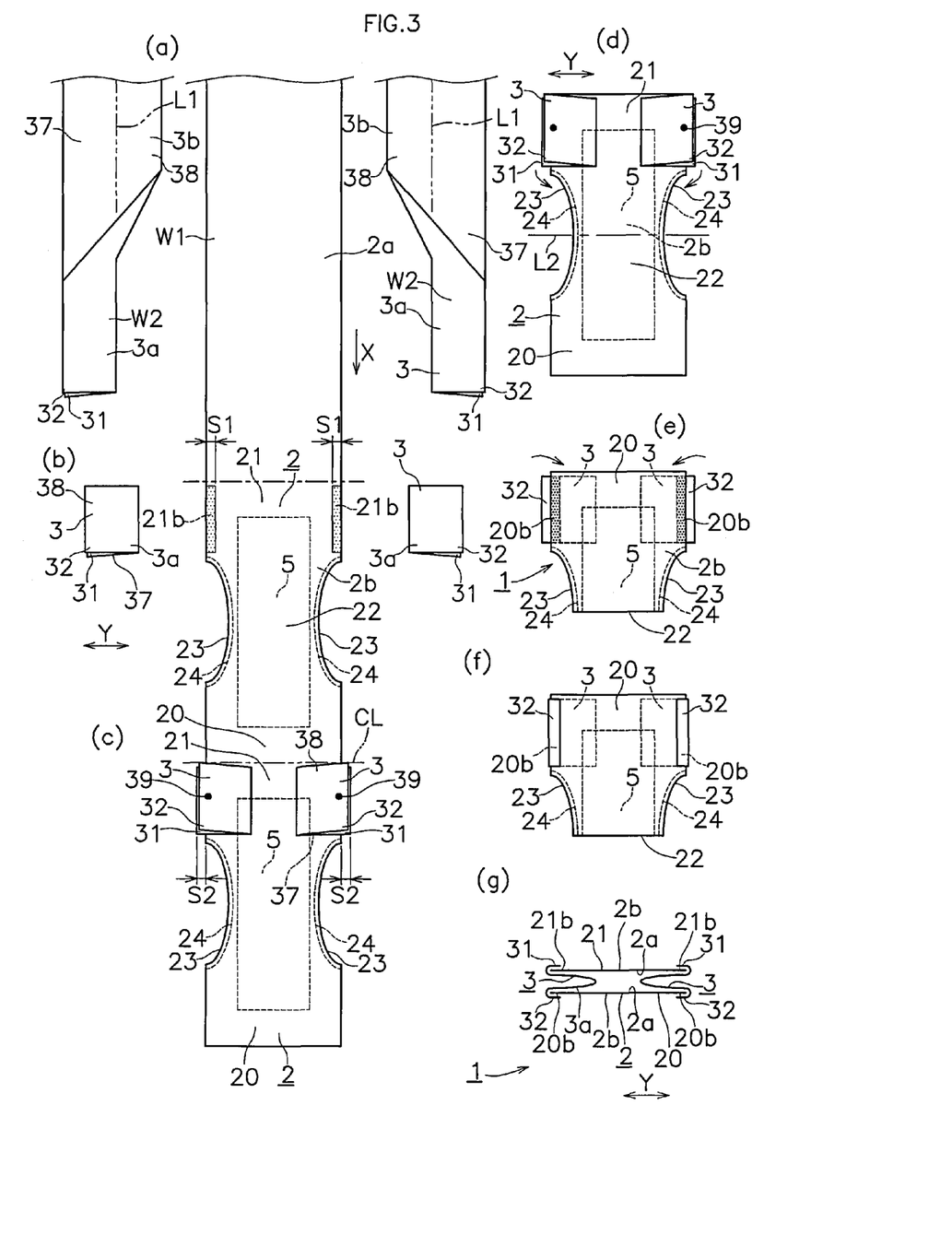
FIGS. 3(a) to 3(f) are schematic front views showing a method for manufacturing a pants-type diaper according to Embodiment 3 of the present invention.
FIG. 3(g) is a schematic cross-sectional view showing the pants-type diaper.

FIG. 3 shows Embodiment 3.

A pants-type diaper of Embodiment 3 is formed so that the side panels 3 are sandwiched between the front portion 20 and the back portion 21 of the diaper body 2, as shown in FIGS. 3(f) and 3(g). The first and second end portions 31 and 32 of the side panels 3 are folded back onto, and attached to, the outer side of end portions 21b of the back portion 21 and the outer side of end portions 20b of the front portion 20 of the diaper body 2 respectively.

The diaper manufacturing method will now be described.

Step of Carrying Diaper Body 2:

As shown in FIG. 3(a), the diaper bodies 2 are carried in the form of a first continuous web W1 in which a plurality of diaper bodies 2 are not separated from one another.

First Folding Step:

On the other hand, the side panels 3 are separately carried in the form of a pair of second continuous webs W2 each including a plurality of side panels 3 not separated from one another.

The side panel 3 is folded along the first line L1 extending in the carrying direction X so that the non-skin-contact surfaces 3b of the side panels 3 face each other.

Then, as shown in FIG. 3(b), the second continuous web W2 is cut into individual side panels 3 which are carried with a predetermined interval therebetween.

First Attachment Step:

On the other hand, an adhesive is applied on the opposing side edge portions 21b of the back portion 21 of the diaper body 2 on the side of an outer surface 2b.

Then, as shown in FIG. 3(c), portions near the first end portions 31 of the pair of side panels 3 are placed on the skin-contact surface 2a of the back portion 21 of the diaper body 2. In this process, the side panels 3 are placed on the diaper body 2 so that the first and second end portions 31 and 32 of the side panels 3 protrude from the side edge portions, opposing each other in the girth direction Y, of the diaper body 2.

The side panels 3 are placed with the first end portions 31 protruding from the diaper body 2 in the girth direction Y by a length S2 (FIG. 3(c)) that is generally equal to a length S1 in the girth direction Y over which the adhesive is applied in FIG. 3(b), i.e., the gluing margin S1.

Tentative Fastening Step:

Immediately after the placement, the first portion 37 and the second portion 38 are tentatively fastened with each other at the tentatively-fastened portion 39 to thereby prevent them from slipping out of place with respect to the diaper body 2, and the side panels 3 are tentatively fastened to the diaper body 2 at the tentatively-fastened portion 39 to thereby maintain the folded state of the side panels 3.

Then, the first continuous web W1 is cut into individual diaper bodies 2 as shown in FIG. 3(c) along the cut-off line CL generally parallel to the girth direction Y.

Second Folding Step:

Then, as shown in FIG. 3(d), the first end portions 31 of the side panels 3 are folded back onto the non-skin-contact surface 2b of the diaper body 2 as indicated by arrows, and the first end portions 31 are attached to the opposing side edge portions 21b of the diaper body 2.

On the other hand, the diaper body 2 is folded in two along the second line L2 extending along the girth direction Y.

Second Attachment Step:

Then, after an adhesive is applied on the opposing side edge portions 20b of the front portion 20 of the diaper body 2 on the side of the non-skin-contact surface 2b shown in FIG. 3(e), the second end portions 32 are folded back onto the non-skin-contact surface 2b of the diaper body 2 as indicated by arrows in FIG. 3(e), thus attaching the second end portions 32 to the diaper body 2 as shown in FIG. 3(f).

That is, the second end portions 32 of the pair of side panels 3 are attached to the front portion 20, to which the side panels 3 have not been attached in the first attachment step.

Thus, the folded-back first and second end portions 31 and 32 of the side panels 3 are attached to the diaper body 2 in the first and second attachment steps, respectively.

A pants-type diaper manufactured by the manufacturing method described above is in a compact state where the side panels 3 are sandwiched between the front portion 20 and the back portion 21 as shown in FIGS. 3(f) and 3(g).

When wearing the diaper, the folded portions of the side panels 3, which are folded along the first line L1, are flipped back so that it is easier to put the legs through.

Other than this, the configuration is similar to that of Embodiment 2, and like elements are denoted by like reference numerals and will not be described below.

Embodiment 4

Another method for manufacturing the pants-type diapers of Embodiments 1 to 3 described above will now be described. Now, another method for manufacturing the pants-type diaper of Embodiment 1 will be described by way of an example.

Figure 4:
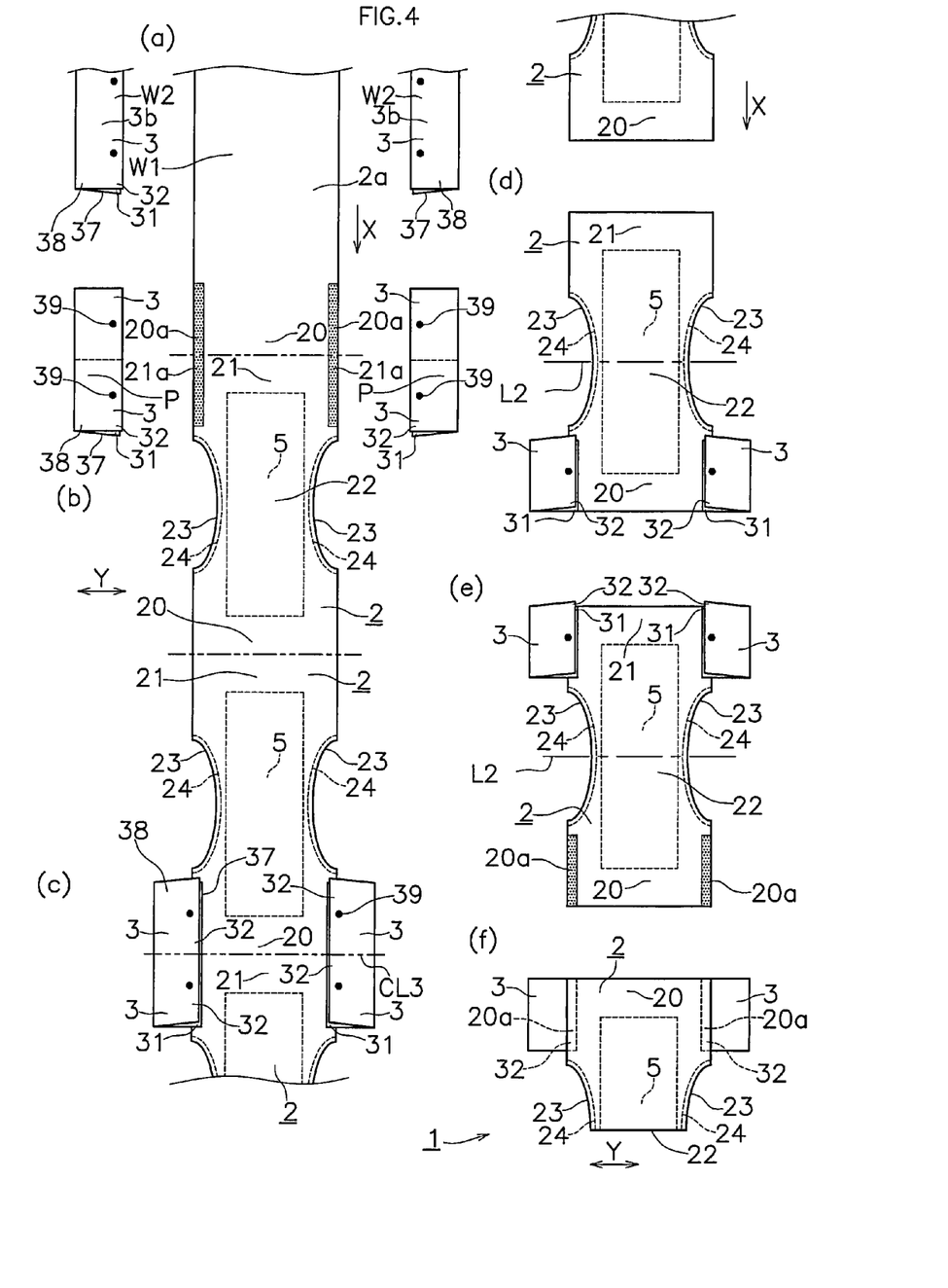
FIGS. 4(a) to 4(f) are schematic front views showing a method for manufacturing a pants-type diaper according to Embodiment 4 of the present invention.

FIG. 4 shows Embodiment 4.

Step of Carrying Diaper Body 2:

As shown in FIG. 4(a), the diaper bodies 2 are carried in the form of a first continuous web W1 in which a plurality of diaper bodies 2 are not separated from one another.

First Folding Step:

On the other hand, the side panels 3 are separately carried in the form of a pair of second continuous webs W2 each including a plurality of side panels 3 not separated from one another.

The side panel 3 is folded so that the skin-contact surfaces 3a thereof face each other. The opposing side panels 3 are folded so that their first and second end portions 31 and 32 are closer to the diaper body 2.

Tentative Fastening Step:

In order to maintain the folded state of the side panel 3 which has been folded in the first folding step, the first portion 37 and the second portion 38 of the side panel 3 are tentatively fastened together by heat seal, or the like, for example, at a tentatively-fastened portion 39.

Then, as shown in FIG. 4(b), the tip portion of the second continuous web W2 in the carrying direction X is cut off one after another. That is, it is cut into continuous panels P, each including two side panels 3 and 3 to be attached to diaper bodies 2 of the first continuous web W1 that are adjacent to each other.

First Attachment Step:

On the other hand, an adhesive is applied on the opposing side edge portions 21a and 20a of the back portion 21 and the front portion 20 of the adjacent diaper bodies 2 on the side of the skin-contact surface 2a, and the continuous panels P are placed on the adjacent diaper bodies 2 as shown in FIG. 4(c). As the continuous panels P are placed on the diaper bodies 2, the first end portions 31 of the pair of continuous panels P are attached to the side edge portions 20a and 21a, opposing each other in the girth direction Y, of the front portion 20 and the back portion 21 of the diaper body 2. In the attachment process, the opposing continuous panels P are projecting from the diaper body 2 in the girth direction Y.

Then, the first continuous web W1 is cut into individual diaper bodies 2 as shown in FIG. 4(d) along a third line (cut-off line) CL3 generally parallel to the girth direction Y. The third line CL3 is formed by a line that bisects the continuous panels P (FIG. 4(c)) in the girth direction Y.

The cutting along the third line CL3 produces a diaper body 2 having the side panels 3 attached on the side of the front portion 20 as shown in FIG. 4(d), and a diaper body 2 having the side panels 3 attached on the side of the back portion 21 as shown in FIG. 4(e).

Second Folding Step:

After an adhesive is applied on the opposing side edge portions 20a (21a) of the skin-contact surface 2a on the side of the front portion 20 (or the back portion 21) of the diaper body 2 shown in FIG. 4(e), the diaper body 2 is folded in two along the second line L2 extending along the girth direction Y. The second line L2 is set at a position such that the front portion 20 and the back portion 21 lie on each other (in line symmetry with each other).

Second Attachment Step:

As the diaper body 2 is folded up, the second end portions 32 of the pair of side panels 3 are attached to the side edge portions 20a, opposing each other in the girth direction Y, of the front portion 20 (or the back portion 21) of the diaper body 2.

Thus, the pants-type diaper 1 is formed in which the second end portions 32 (or the first end portions 31) of the side panels 3 are attached to the front portion 20 (or the back portion 21), to which the side panels 3 have not been attached.

INDUSTRIAL APPLICABILITY

The present invention is applicable to a method for manufacturing a pants-type diaper.

DESCRIPTION OF THE REFERENCE NUMERALS

1: Pants-type diaper
2: Diaper body
3: Side panel
20: Front portion
21: Back portion
22: Crotch portion
31: First end portion
32: Second end portion
CL3: Third line
L1: First line
L2: Second line
P: Continuous panel
W1: First continuous web
W2: Second continuous web

The invention claimed is:

1. A method for manufacturing a pants-type diaper comprising: a diaper body including a front portion covering an abdominal side of a wearer, a back portion covering a back side of the wearer, and a crotch portion between the front portion and the back portion; a side panel connecting together, in a girth direction, a first side edge portion of the front portion and a first side edge portion of the back portion with each other; and another side panel connecting together, in the girth direction, a second side edge portion of the front portion which is away from the first side edge portion thereof in the girth direction and a second side edge portion of the back portion which is away from the first side edge portion thereof in the girth direction, the method comprising:

a step of carrying the diaper body in a longitudinal direction perpendicular to the girth direction;

a first folding step of folding each of the side panels along a virtual first line extending in the longitudinal direction so that a first portion and a second portion of each of the side panels lie on each other;

a first attachment step of attaching a first end portion of each of the side panels in the girth direction to the first and second side edge portions of the front portion or attaching the first end portion of each of the side panels in the girth direction to the first and second side edge portions of the back portion;

a second folding step of folding the diaper body along a virtual second line extending along the girth direction so that the front portion and the back portion lie on each other; and a second attachment step of attaching a second end portion of each of the side panels away from the first end portion thereof in the girth direction to the first and second side edge portions of the back portion, to which each of the side panels is unattached in the first attachment step or attaching the second end portion of each of the side panels to the first and second side edge portions of the front portion, to which each of the side panels is unattached in the first attachment step, wherein each of the side panels is folded in the first folding step so that non-skin-contact surfaces thereof face each other; and each of the side panels is attached to the front portion and the back portion in the first and second attachment steps so that at least a portion of each of the side panels between the first end portion and the second end portion is sandwiched between the front portion and the back portion, the method further comprising: a step of placing each of the side panels on the diaper body so that the first and second end portions of each of the side panels folded in the first folding step protrude from each of the side edge portions of the diaper body in the girth direction;

a step of folding back the first end portion of each of the side panels so that the first end portion each lies on the first and second side edge portions of a non-skin-contact surface of the diaper body in the girth direction; and a step of folding back the second end portion of each of the side panels so that the second end portion each lies on the first and second side edge portions of the non-skin-contact surface of the diaper body in the girth direction, wherein, after the second folding step of folding the diaper body, the folded-back first end portion is unremovably attached to the non-skin contact surface of the diaper body in the first attachment step and the folded-back second end portion is unremovably attached to the non-skin contact surface of the diaper body in the second attachment step.

2. The method for manufacturing a pants-type diaper according to claim 1, wherein:

the diaper bodies are carried in a form of a first continuous web in which a plurality of diaper bodies are unseparated from one another;

the side panels are carried in a form of a second continuous web in which a plurality of side panels are unseparated from one another;

the second continuous web is cut into a continuous panel including two side panels continuous with each other which are to be attached to the diaper bodies adjacent with each other in the first continuous web;

the cut-off continuous panel is attached to the first continuous web; and the first continuous web is cut, together with the continuous panel, along a virtual third line, which bisects the continuous panel in the girth direction, so as to cut the first continuous web into individual diaper bodies.

3. The method for manufacturing a pants-type diaper according to claim 1, further comprising a tentative fastening step of tentatively fastening together the first portion and the second portion of each of the side panels so as to maintain the folded state of each of the side panels folded in the first folding step as well as each of the side panels is tentatively fastened to the diaper body to thereby prevent the side panels from slipping out of place with respect to the diaper body, wherein in the tentative fastening step, the first portion and the second portion of each of the folded side panels and the diaper body are tentatively fastened together by a heat seal at an identical area, and the tentative fastening step is carried out after the first folding step and the first attachment step, and before the second folding step.

4. The method for manufacturing a pants-type diaper according to claim 3, wherein:

the diaper bodies are carried in a form of a first continuous web in which a plurality of diaper bodies are unseparated from one another;

the side panels are carried in a form of a second continuous web in which a plurality of side panels are unseparated from one another;

the second continuous web is cut into a continuous panel including two side panels continuous with each other which are to be attached to the diaper bodies adjacent with each other in the first continuous web;

the cut-off continuous panel is attached to the first continuous web; and the first continuous web is cut, together with the continuous panel, along a virtual third line, which bisects the continuous panel in the girth direction, so as to cut the first continuous web into individual diaper bodies.

* * * * *